United States Patent [19]

Arai

[11] Patent Number: 5,117,029

[45] Date of Patent: May 26, 1992

[54] PROCESS FOR PREPARING ALKOXY-FUNCTIONAL ORGANOPOLYSILOXANES AND THE RESULTANT ALKOXY-FUNCTIONAL ORGANOPOLYSILOXANES

[75] Inventor: Masatoshi Arai, Annaka, Japan

[73] Assignee: Shin-Etsu Chemical Company, Limited, Tokyo, Japan

[21] Appl. No.: 741,371

[22] Filed: Aug. 7, 1991

[30] Foreign Application Priority Data

Aug. 8, 1990 [JP] Japan .................. 2-209600

[51] Int. Cl.$^5$ ............................................. C07F 7/08
[52] U.S. Cl. ....................................................... 556/457
[58] Field of Search ............................. 556/457, 458

[56] References Cited

U.S. PATENT DOCUMENTS

| 4,658,006 | 4/1987 | Inoue ............................ 556/457 X |
| 4,717,773 | 1/1988 | Kenney et al. ...................... 556/457 |
| 4,950,726 | 8/1990 | Yoshioka et al. ............... 556/457 X |

Primary Examiner—Arthur C. Prescott
Attorney, Agent, or Firm—Millen, White & Zelano

[57] ABSTRACT

Alkoxy-functional organopolysiloxanes can be prepared in high yields by reacting a hydroxy-containing organic silicon compound with an α-alkoxysilyl ester in the absence of a catalyst. The alkoxy-functional organopolysiloxanes are useful modifiers and surface treating agents a well as raw materials for silicone resins and rubbers.

5 Claims, No Drawings

PROCESS FOR PREPARING ALKOXY-FUNCTIONAL ORGANOPOLYSILOXANES AND THE RESULTANT ALKOXY-FUNCTIONAL ORGANOPOLYSILOXANES

This invention relates to a novel process for preparing alkoxy-functional organopoly-siloxanes and the resultant alkoxy-functional organopolysiloxanes.

BACKGROUND OF THE INVENTION

Alkoxy-functional organopolysiloxanes having an alkoxysilyl group are useful modifiers and surface treating agents for inorganic and organic materials as well as useful raw materials for preparing silicone resins and rubbers of dealcoholysis curing type. In the past, such alkoxy-functional organopoly-siloxanes having an alkoxysilyl group were prepared by effecting condensation reaction between an organosilane having a silanol group or an organosiloxane terminated with a silanol group and an alkoxysilane in the presence or absence of a catalyst such as amines, carboxylic acids, and carboxylates of zinc, tin, iron and similar metals, this process suffered from a problem of low reaction yield in that reaction did not proceed well in the absence of a catalyst and that in the presence of a catalyst, much by-products were formed particularly when the reactant has two or more alkoxy groups in a molecule. With the catalyst present, there arose another problem that removal of the catalyst (amines, carboxylic acids, metal carboxylates and the like) from the reaction product was difficult so that the recovered product contained a substantial proportion of the catalyst as an impurity.

Another known process for preparing organopolysiloxanes having an alkoxysilyl group is by reacting chlorosilane and an organic silicon compound having a silanol group in the presence of a hydrogen halide acceptor such as an amine (see Japanese Patent Application Kokai No. 247756/1986). With this process, there is formed a hydrogen halide acceptor salt which is difficult to remove by stripping or other fractionating means even when it has a low molecular weight, and almost impossible to remove if it has a high molecular weight.

SUMMARY OF THE INVENTION

Therefore, an object of the present invention is to provide a novel and efficient process for preparing an alkoxy-functional organopolysiloxane having an alkoxysilyl group in high yields without inviting the problems of residual catalyst and by-products.

The inventor has found that an α-alkoxysilyl ester compound of the general formula (A):

$$(R^1O)_n-\underset{\underset{R^4}{|}}{\overset{\overset{R^2_{3-n}}{|}}{Si}}-\underset{\underset{R^4}{|}}{\overset{\overset{R^3}{|}}{C}}-COOR^5 \qquad (A)$$

wherein $R^1$, $R^4$, and $R^5$ are independently selected from substituted or unsubstituted monovalent hydrocarbon groups free of an aliphatic unsaturated bond, $R^2$ is a substituted or unsubstituted monovalent hydrocarbon group, $R^3$ is a hydrogen atom or methyl group, and letter n is an integer of 1, 2 or 3 is effective in reacting with an equimolar amount of a silanol group in a catalyst-free system to form an alkoxysilyl group.

Therefore, the present invention provides a process for preparing an alkoxy-functional organopolysiloxane by reacting a hydroxyl-containing organic silicon compound with an at least equimolar amount per mol of the hydroxyl group of said compound of an organic silicon compound of formula (A). The present invention also provides the alkoxy-functional organopolysiloxane obtained by this process.

DESCRIPTION OF THE PREFERRED EMBODIMENTS

The first reactant used in the process of the present invention is a hydroxyl-containing organic silicon compound which may be selected depending on a desired end product. It may be of either high or low molecular weight and either straight chain or cyclic or branched. As to its form, it may be liquid or resinous at room temperature. Typical and commercially widely used examples are organo(poly)siloxanes terminated with a hydroxyl group of the general formula (B):

$$HO(\underset{\underset{R^6}{|}}{\overset{\overset{R^6}{|}}{Si}}O)_mH \qquad (B)$$

wherein $R^6$ is a substituted or unsubstituted monovalent hydrocarbon group, and m is an integer of from 1 to 10,000. Preferably, $R^6$ is a substituted or unsubstituted monovalent hydrocarbon group having 1 to 10 carbon atoms, more preferably 1 to 8 carbon atoms, for example, alkyl groups such as methyl, ethyl, propyl, and butyl; alkenyl groups such as vinyl and allyl; aryl groups such as phenyl and tolyl; aralkyl groups such as benzyl and 2-phenylethyl; and substituted ones of these groups in which some or all of the hydrogen atoms are replaced by halogen atoms or the like, such as chloromethyl and 3,3,3-trifluoropropyl groups. Several illustrative, non-limiting examples of the hydroxyl-containing organic silicon compound are given below. In the formulae, Me is methyl and Ph is substituted or unsubstituted phenyl.

$$Me_3SiOH, HOSiOH, PhSi(OH)_3,$$
$$\underset{Ph}{\overset{Ph}{|}}$$

$$Me_3Si(OSi)_3OSiMe_3, MePhSiOH,$$
$$\underset{OH}{\overset{Me}{|}}$$

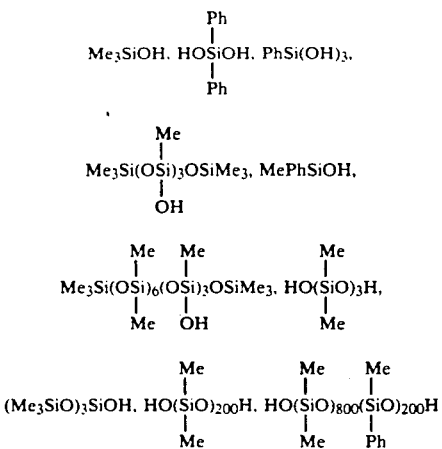

The second reactant used in the process of the present invention is an organic silicon compound or α-alkoxysilyl ester of the general formula (A):

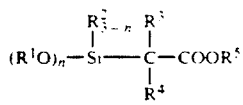

(A)

wherein $R^1$, $R^4$, and $R^5$, which may be the same or different, are independently selected from substituted or unsubstituted monovalent hydrocarbon groups free of an aliphatic unsaturated bond, $R^2$ is a substituted or unsubstituted monovalent hydrocarbon group as defined for $R^6$, preferably a methyl or vinyl group, $R^3$ is a hydrogen atom or methyl group, and letter n is an integer of 1, 2 or 3.

The monovalent hydrocarbon groups free of an aliphatic unsaturated bond represented by $R^1$, $R^4$, and $R^5$ include hydrocarbon groups having 1 to 10 carbon atoms, preferably 1 to 8 carbon atoms, for example, alkyl groups such as methyl, ethyl, propyl, and butyl; aryl groups such as phenyl and tolyl; aralkyl groups such as benzyl and 2-phenylethyl; and substituted ones of these groups in which some or all of the hydrogen atoms are replaced by halogen atoms or the like, such as chloromethyl and 3,3,3-trifluoropropyl groups.

Several illustrative, non-limiting examples of the organic silicon compound of formula (A) are given below. In the formulae, Me is methyl, Et is ethyl, Bu is butyl, and Ph is substituted or unsubstituted phenyl.

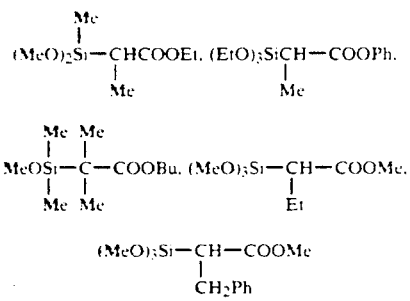

The organic silicon compounds of formula (A) may be readily synthesized by heating an alkoxyhydrosilane and an acrylate ester in the presence of a platinum catalyst to effect addition reaction according to the following reaction scheme.

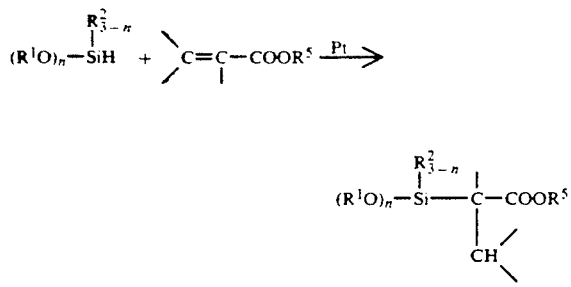

In the practice of the present invention, the first and second reactants, that is, a hydroxyl-containing organic silicon compound and an organic silicon compound of formula (A) are mixed for reaction. The organic silicon compound of formula (A) reacts with a silanol group (1) of the hydroxyl-containing organic silicon compound to form an alkoxysiloxane bond (2) and an alkyl ester (3) as a by-product according to the following reaction scheme.

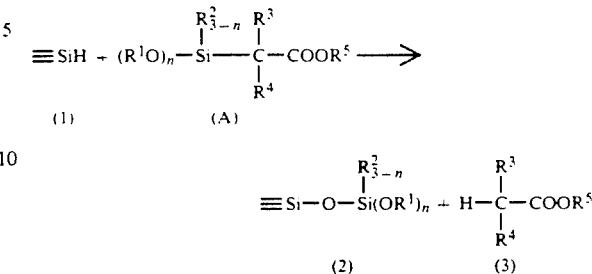

This reaction usually proceeds in the absence of a catalyst. That is, effective reaction takes place simply by mixing the first and second reactants. From a stoichiometry aspect, the reaction requires an organic silicon compound of formula (A) in an equimolar or more amount per mol of the hydroxyl group. Therefore, at least equimolar amount, preferably 1 to 1.5 mol per mol of the hydroxyl group of an organic silicon compound of formula (A) is mixed with the hydroxyl-containing organic silicon compound for reaction to take place.

When the hydroxyl-containing organic silicon compound as the first reactant is a compound of formula (B), at least 2 mol of the compound of formula (A) is used per mol of the compound of formula (B). Then there is formed an alkoxy-functional organopolysiloxane having an alkoxysilyl group at either end of the general formula (C):

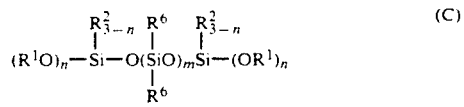

(C)

wherein $R^1$, $R^2$, $R^6$, m and n are as defined above.

Reaction conditions are not particularly limited. Often, a mixture of the first and second reactants is heated at 50° to 150° C., more preferably 80° to 90° C. for about 1 to 20 hours, more preferably about 4 to 5 hours. A reaction medium such as toluene, benzene and xylene may be used. The reaction forms an alkyl ester by-product as well as the end product. The by-product may be readily removed by heating or stripping in conventional manner or may be left in the product as the case may be.

There has been described a process for efficiently preparing an alkoxy-functional organopolysiloxane having an alkoxysilyl group from an organic silicon compound having a hydroxyl group in a catalyst-free system in high yields. The resulting alkoxy-functional organopolysiloxanes having an alkoxysilyl group are useful as modifiers and surface treating agents for inorganic and organic materials and as source materials for preparing silicone resins and rubbers of dealcoholysis curing type.

EXAMPLE

Examples of the present invention are given below by way of illustration and not by way of limitation.

EXAMPLE 1

A reactor equipped with a stirrer, thermometer and condenser was charged with 91 grams (0.1 mol) of trimethylsilanol and 22.2 grams (0.1 mol) of ethyl α- trimethoxy-silylpropionate. Reaction was effected under reflux for 3 hours.

At the end of reaction, 1,1,1-trimethyl-3,3,3-trimethoxydisiloxane having a boiling point of 150° to 152° C./760 mmHg was collected by distillation in a yield of 95%. The structure of the reaction product was identified by NMR and gas mass spectroscopy.

EXAMPLE 2

A reactor as used in Example 1 was charged with 1,000 grams of dimethylpolysiloxane terminated with a hydroxyl group at either molecular chain end having a viscosity of 5,100 centistokes at 25° C. (OH value 0.0070 mol/100 grams) and 22.2 grams (0.084 mol) of ethyl α-triethoxysilylpropionate. Reaction was effected at 90° C. for 5 hours.

At the end of reaction, excess ethyl α-triethoxysilylpropionate and ethyl propionate by-product were removed by stripping at 120° C./2 mmHg, obtaining 980 grams of a colorless clear oily product having a viscosity of 5,300 centistokes at 25° C.

To 100 grams of the oily product was added 0.1 gram of a 50% toluene solution of dibutyltin dioctoate. The oily product cured tack-free within 5 minutes at 20° C. and RH 50%.

For comparison purposes, 0.1 gram of a 50% toluene solution of dibutyltin dioctoate was added to 100 grams of the starting reactant, hydroxyl-terminated dimethylpolysiloxane having a viscosity of 5,100 centistokes at 25° C. The material remained tacky after 24 hours.

EXAMPLE 3

A reactor as used in Example 1 was charged with 1,000 grams of a 50% toluene solution of a co-hydrolyzate of trimethylchlorosilane and tetraethoxysilane (M/Q=0.70, OH value 0.011 mol/100 grams of resin) and 8.7 grams (0.033 mol) of ethyl α-triethoxysilylpropionate. Reaction was effected at 90° C. for 5 hours.

At the end of reaction, 0.1 gram of dibutyltin dimethoxide was added to 100 grams of the reaction solution. The solution was cast on a glass plate to a thickness of about 0.5 mm and cured at room temperature for 24 hours. There was formed a hard film which was insoluble in toluene.

For comparison purposes, 0.1 gram of dibutyltin dimethoxide was added to 100 grams of the co-hydrolyzate toluene solution. The solution was cast on a glass plate and cured at room temperature for 24 hours. There was formed a hard film which was dipped in toluene, finding that the film was dissolved away.

Although some preferred embodiments have been described, many modifications and variations may be made thereto in the light of the above teachings. It is therefore to be understood that within the scope of the appended claims, the invention may be practiced otherwise than as specifically described.

I claim:

1. A process for preparing an alkoxy-functional organopolysiloxane, comprising the step of:
   reacting a hydroxyl-containing organic silicon compound with an at least equimolar amount per mol of the hydroxyl group of said compound of an organic silicon compound of the general formula (A):

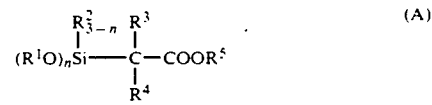

wherein $R^1$, $R^4$, and $R^5$ are independently selected from substituted or unsubstituted monovalent hydrocarbon groups having 1 to 10 carbon atoms free of an aliphatic unsaturated bond, $R^2$ is a substituted or unsubstituted monovalent hydrocarbon group having 1 to 10 carbon atoms, $R^3$ is a hydrogen atom or methyl group, and letter n is an integer of 1, 2 or 3.

2. The process of claim 1 wherein said hydroxy-containing organic silicon compound has the general formula (B):

wherein $R^6$ is a substituted or unsubstituted monovalent hydrocarbon group having 1 to 10 carbon atoms, and m is an integer of from 1 to 10,000, whereby an alkoxy-functional organopolysiloxane of the general formula (C):

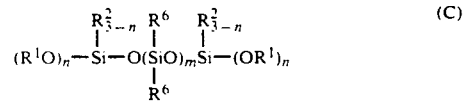

wherein $R^1$, $R^2$, $R^6$, m and n are as defined above is obtained.

3. The process of claim 1 wherein the reaction is conducted at a temperature of 50° to 150° C. for about 1 to 20 hours.

4. The process of claim 1 wherein the reaction is conducted in the presence of a solvent selected from the group consisting of toluene, benzene and xylene.

5. An alkoxy-functional organopolysiloxane obtained by the process of claim 2 having general formula (C):

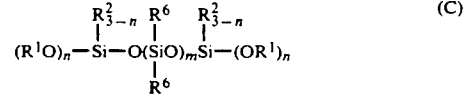

wherein $R^1$, $R^2$, $R^6$, m and n are as defined above.

* * * * *